United States Patent [19]

Fletcher

[11] 3,990,443

[45] Nov. 9, 1976

[54] DROP RATE SENSING AND REGULATING APPARATUS

[75] Inventor: John H. Fletcher, Stamford, Conn.

[73] Assignee: Data Service Co. of America, Inc., Norwalk, Conn.

[22] Filed: Oct. 14, 1975

[21] Appl. No.: 622,508

[52] U.S. Cl. ............................... 128/214 E; 73/204; 128/DIG. 13; 137/486; 137/487.5; 222/54; 340/239 R
[51] Int. Cl.² ......................................... A61M 5/16
[58] Field of Search ......... 128/214 C, 214 E, 214 F, 128/214.2, 227, DIG. 12, DIG. 13; 222/54, 420; 137/486, 487.5; 73/204; 340/239 R

[56] References Cited
UNITED STATES PATENTS

| 3,390,577 | 7/1968 | Phelps et al. ................. 128/214 E X |
| 3,500,366 | 3/1970 | Chesney et al. .................... 340/222 |
| 3,655,095 | 4/1972 | Kienitz ......................... 128/214 E X |
| 3,790,042 | 2/1974 | McCormick et al. ....... 128/214 E X |
| 3,832,998 | 9/1974 | Gregg ............................. 128/214 E |
| 3,871,229 | 3/1975 | Fletcher ..................... 128/214 E X |

*Primary Examiner*—Dalton L. Truluck
*Attorney, Agent, or Firm*—St. Onge Mayers Steward & Reens

[57] ABSTRACT

An apparatus, for example, an intravenous drop-feed apparatus for sensing the rate at which liquid drops fall along a predetermined vertical path and for regulating this drop rate to be substantially equal to a preselected drop rate includes a disposable drip chamber which defines a vertical drop path. The drip chamber is formed with an indentation having an upper wall that projects into the drop path to be impinged by drops falling on its interior surface. A probe is removably mounted on the outside of the chamber in interfitting engagement with the chamber indentation and includes an electrically conductive element located to contact the exterior surface of the upper indentation wall. The element, which is electrically but not thermally isolated from falling drops, exhibits conductivity that varies significantly with its temperature and, accordingly, generates pulses at a rate that corresponds to the periodic rate of the falling drops. These pulses are compared with the preselected rate, which may be adjustable, and any detected difference is used to regulate liquid back pressure in the chamber to, in turn, regulate the drop rate. A clamping assembly, which reduces the flow area of a tube which conducts liquid from the drip chamber, is controlled by a heat sensitive bimetallic element to regulate this back pressure.

20 Claims, 12 Drawing Figures

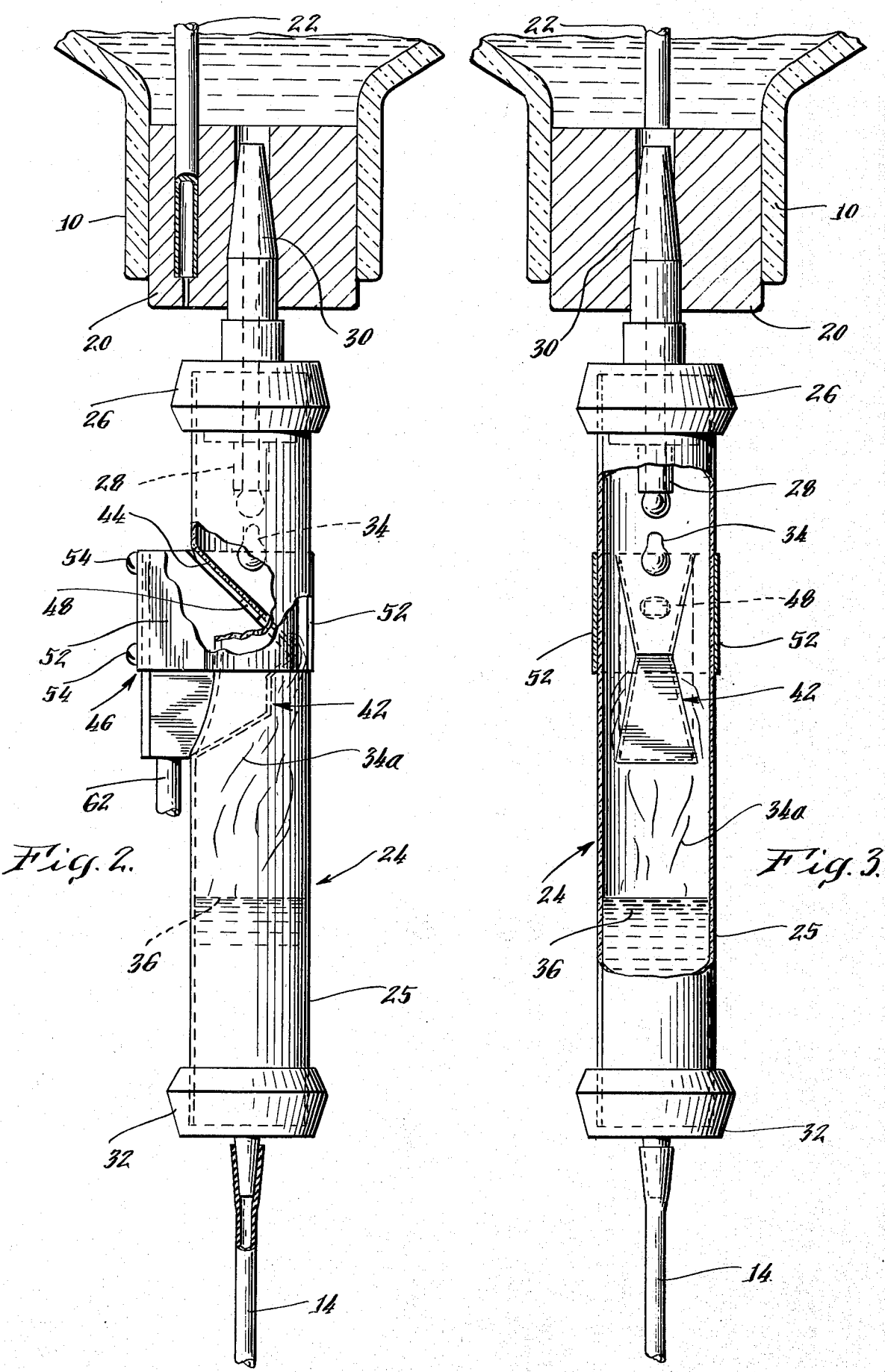

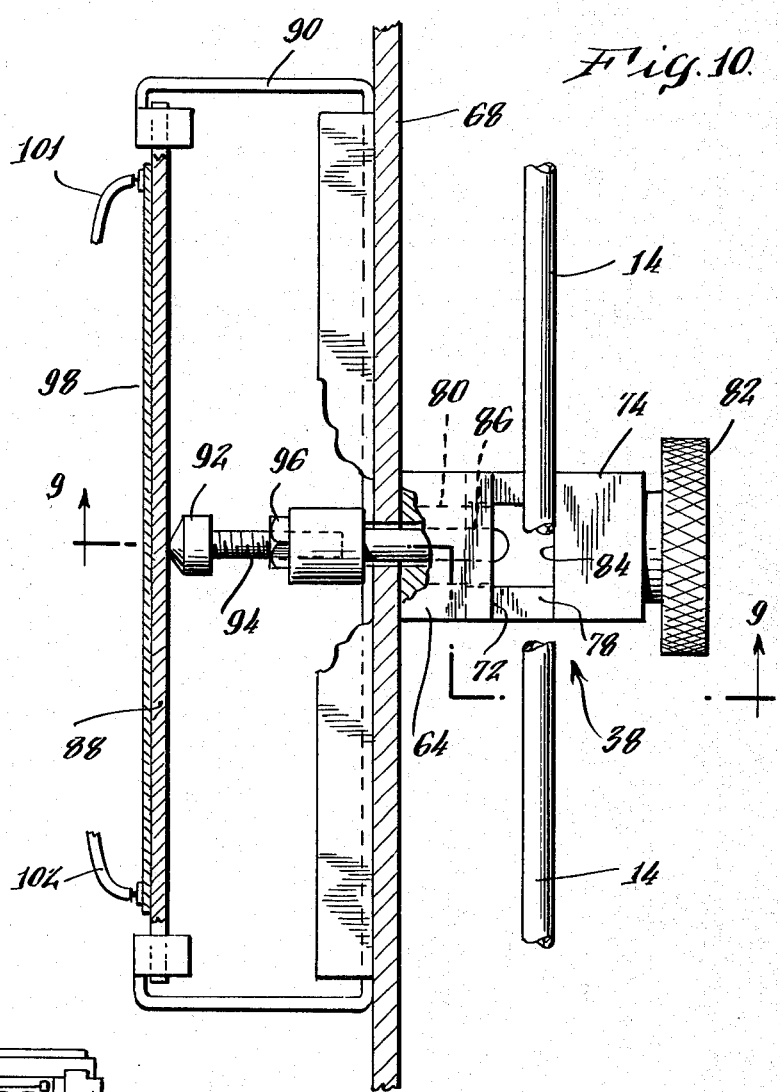
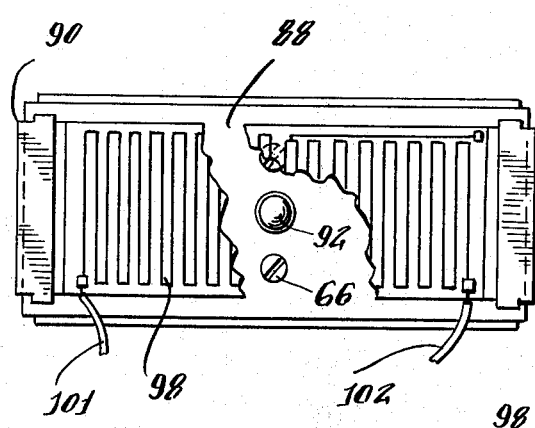
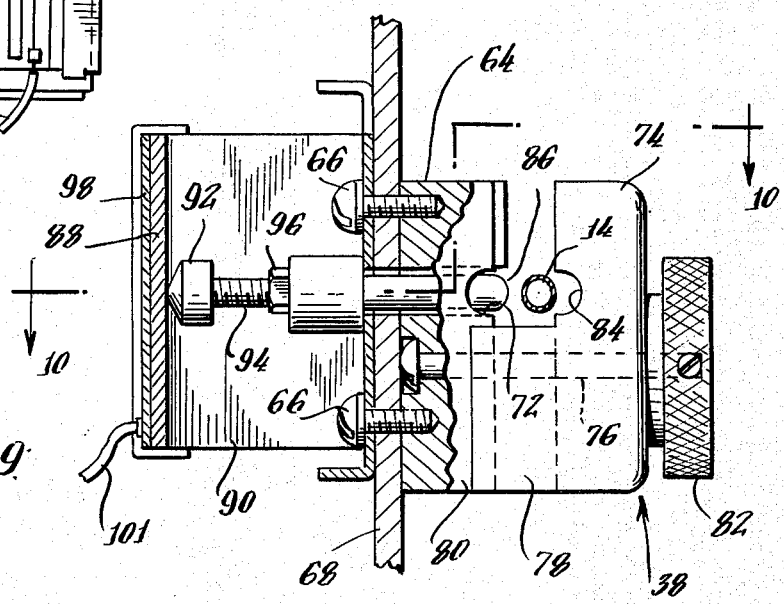

DROP RATE SENSING AND REGULATING APPARATUS

BACKGROUND OF THE INVENTION

1. Field of the Invention

The present invention relates to an apparatus for sensing and regulating drop-by-drop flow of liquid. This apparatus has particular value as a medical instrument for automatically sensing and controlling drop-feed of liquids where accuracy is of considerable importance.

2. Description of the Prior Art

In the medical field, drop-by-drop liquid feed systems are commonly used to control introduction of liquids, such as whole blood, liquid plasma, or liquid nutrients, into a patient. A typical intravenous liquid injection system comprises a bottle of liquid supported in an inverted position, an intravenous feed tube connected indirectly to the inverted bottle opening and a valve mechanism such as a manually adjustable clamp that controls the rate at which liquid is allowed to leave the bottle. A transparent drip chamber is ordinarily interposed between the bottle and the feed tube so that a nurse or other attendant can observe the rate at which liquid drops out of the bottle. A pool of liquid is also maintained in the lower portion of the chamber to ensure that no air enters the feed tube or is conducted to the patient.

Various devices for automatically controlling the rate at which liquid drops into the drip chamber have been proposed. For example, U.S. Pat. No. 3,871,229 to John H. Fletcher, inventor of the subject invention, discloses a drop sensing apparatus which comprises a thermally responsive probe sensor mounted inside the drip chamber and electrically insulated from the drop stream. However, the sensor is thermally coupled to the stream to generate pulses at a rate corresponding to the periodicity of the falling drops. The sensed rate is compared with an adjustable preselected rate and any detected difference is utilized to regulate the drop rate. Regulation is accomplished by a motor driven adjustable clamp which variably crimps the feed tube to regulate liquid back pressure in the drip chamber and, in turn, to regulate the drop rate.

This system is high resistant to self-induced failure and to error due to spurious signals yet is highly accurate. Therefore, it is superior to previously devised automatic systems which employ photocell drop sensors (see, for example U.S. Pat. Nos. 3,736,930 (Georgi) and 3,700,904 (Stobbe et al.)), or capacitive drop sensors (see, for example U.S. Pat. Nos. 3,390,577 (Phelps et al.) and 3,545,271 (Amir et al.)) for controlling the rate of liquid flow. Generally, photocell drop sensors are expensive and are subject to inaccuracy which results from extraneous light signals from, for example, a flickering fluorescent light. Moreover, the drip chamber may accummulate deposits of residue on its side walls that obstruct the light beam which actuates the sensor. Capacitive systems exhibit many of the same drawbacks for similar reasons.

However, the advantages provided by the system disclosed in the Fletcher Patent over other prior systems may be even farther improved and enhanced by the present invention.

Motor driven drop rate controls (see, for example, the Fletcher and Stobbe et al. patents), though well suited for many applications, are also generally expensive and have certain other drawbacks which the present invention is intended to eliminate.

SUMMARY OF THE INVENTION

In a preferred embodiment, to be described below in detail, the drop-rate sensing and regulating apparatus of the present invention is exceptionally accurate as well as highly resistant to self-induced failure and to error which might result from extraneous signals. This invention further provides automated electronic control of a liquid drop rate and operates at a very low, non-lethal electrical potential. Moreover, all of the electrical components of this apparatus are completely isolated from contact with the liquid being monitored. In addition to these advantageous aspects, this apparatus incorporates several additional features which make it extremely practical as well as convenient for widespread use in the medical fields. In particular, the drop sensing apparatus is designed so that its electrical components are repeatedly reusable even after its liquid handling components require replacement. Further, the drop rate regulating portion of this invention is simple, inexpensive, yet is extremely reliable.

Generally, the apparatus of the present invention senses the rate at which liquid drops fall along a predetermined vertical path and regulates this drop rate to be substantially equal to a preselected drop rate. The apparatus includes a disposable drip chamber which defines a vertical drop path and which is formed with an indentation having an upper wall that projects into the drop path to be impinged on its interior surface by falling drops. A probe is removably mounted on the outside of the chamber in interfitting engagement with the chamber indentation and includes an electrically conductive element located to contact the exterior surface of the upper indentation wall. The conductive element, which is electrically but not thermally isolated from the falling drops by the indentation wall, exhibits conductivity that varies significantly with its temperature and, accordingly, generates pulses at a rate which corresponds to the periodic rate of the falling drops.

The pulses generated by the conductive element are compared electronically with the predetermined drop rate and any difference detected is used to regulate liquid back pressure in the chamber to regulate, in turn, the drop rate. The liquid back pressure in the chamber is controlled by a clamping assembly which reduces the flow area of the feed tube that conducts liquid from the drip chamber. This clamping assembly is operated by a bimetallic element which is operatively associated with a heat applying coil. When the coil is heated, in response to any detected discrepancy between the actual and the desired drop rate, the bimetallic strip is caused to flex in a preselected direction until the discrepancy is eliminated.

The preselected drop rate may be set by the operator of the system at the time it is put into operation. Thus, this system may be operated over a wide range of liquid flow rates required by various applications.

Accordingly, it is an object of the present invention to provide an apparatus for sensing and regulating the rate at which liquid drops fall along a predetermined vertical path in a highly accurate, efficient manner. The drip chamber incorporated in this apparatus may be replaced without destroying any electrical components of the system. Moreover, the drop rate is controlled by a simple as well as reliable device.

Other objects, aspects, and advantages of the present invention will be pointed out in, or will be understood from the following detailed description provided below in conjunction with the accompanying drawings.

BRIEF DESCRIPTION OF THE DRAWINGS

FIGS. 2 and 3 are enlarged side elevational views, shown partly in cross-section, of the disposable drip chamber assembled with the removable electrically conductive sensor probe.

FIG. 9 is a side elevational view, shown partly in cross-section taken through discontinuous plane 9-9 in FIG. 10, of the clamping assembly and the bimetallic actuator for adjustably crimping the feed tube which conducts fluid away from the drip chamber.

FIG. 10 is a top elevational view, shown partly in cross-section taken through discontinuous plane 10-10 in FIG. 9, of this clamping assembly.

FIG. 11 is a rear elevational view, partly broken away to show detail, of the bimetallic actuator and of the heat applying coil attached to the actuator.

DETAILED DESCRIPTION OF THE PREFERRED EMBODIMENT

Figure 1:
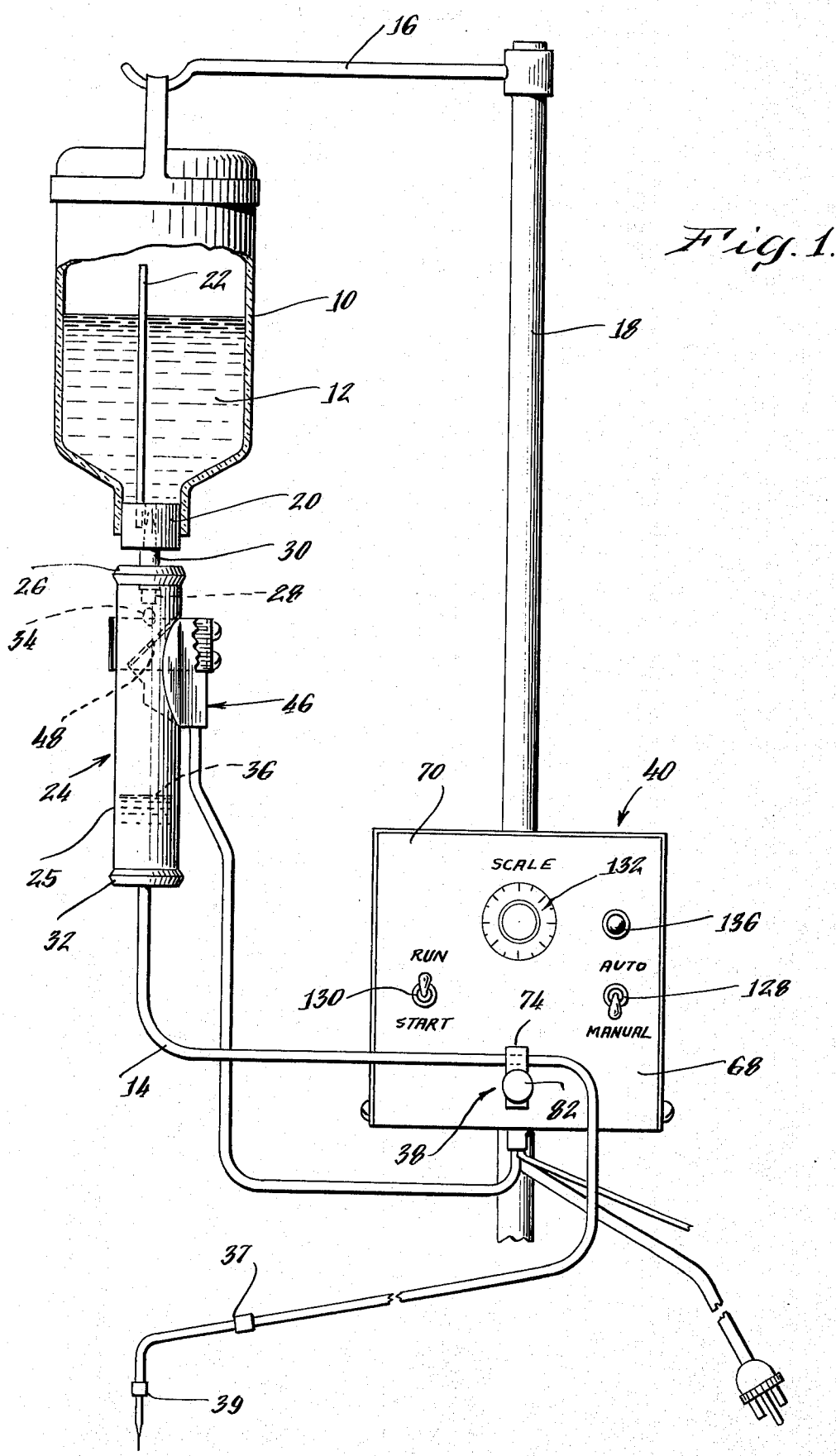
FIG. 1 is a frontal view shown partly in cross-section of the various components of the apparatus of the present invention for sensing the rate at which liquid drops fall along a predetermined vertical path and for regulating this drop rate to be substantially equal to a preselected drop rate.

FIG. 1 illustrates the various components of the apparatus of the present invention for sensing and regulating the rate at which liquid drops fall along a predetermined vertical path. This apparatus operates in conjunction with a bottle 10 which contains a liquid 12, such as whole blood, liquid plasma, or liquid nutrient, to be supplied intravenously to a patient through a flexible, pliable feed tube 14. The bottle 10 is supported in an inverted position from an outwardly extending arm 16 mounted on a support standard 18. The mouth of the bottle 10 is closed by a stopper 20 which also holds an air vent tube 22.

A drip chamber assembly, generally indicated at 24 and designed to be disposable in a fashion described below in detail, is mounted below and in fluid communication with the interior of bottle 10. This drip chamber assembly comprises a generally cylindrical, transparent body portion 25 and an upper cap member 26 provided with a drop forming station 28. A continuous channel extends from station 28 upwardly into a "spike" 30 that is pressed into stopper 20 to be held therein. A lower cap 32, to which intravenous feed tube 14 is connected, is mounted at the lower end of the drip chamber body 24. All of these components of the drip chamber may be made of a suitable material such as injection or blow molded plastic. The intravenous feed tube 14 is ordinarily attached to a fixed injection site 37 which terminates in a needle adaptor 39. An appropriately selected needle is connected to adaptor 39 and ultimately introduced into the vein of the patient by a skilled attendant.

During operation of the apparatus, liquid drops 34 are successively formed at the drop forming station 28 and fall one at a time to the bottom of the drip chamber where they produce a liquid pool 36. Liquid is then conducted from the pool into the intravenous feed tube 14 for ultimate delivery to the patient.

The rate at which liquid is fed from pool 36 is controlled by a regulating clamp assembly, generally indicated at 38, which is operated by an intravenous drop tube or I.D.T. monitor, generally indicated at 40. (The clamp assembly and monitor will be described in greater detail at a later point.) As is known in the art, control of the rate at which liquid leaves pool 36, in turn, controls the back pressure in drip chamber 24 and thus governs the rate of formation of drops 34 at drop forming station 28.

The present invention is concerned with a novel design for sensing the rate at which drops fall through drip chamber 24. Specifically, the drip chamber is designed to be economically manufactured yet to be disposable after use. The sensor for sensing the rate of drop fall is mounted entirely on the exterior of drop chamber 24 and can be detached therefrom so that the sensor need not be replaced when the drip chamber is. The present invention further concerns an improved means for controlling the rate at which drops fall in drip chamber 24 in an economical, simple, yet reliable manner.

A. The Disposable Drip Chamber and Drop Rate Sensor Assembly

As shown in FIGS. 2 and 3, the upper portion of the body 25 of drip chamber assembly 24 is formed with an indentation 42 in its side wall. This indentation is irregular, being generally M-shaped in side elevation and includes a downwardly inclined upper wall 44 which projects to a position directly beneath drop forming station 28. Accordingly, upper wall 44 is directly in the path of drops falling through drip chamber 24 when chamber body 25 is positioned in a generally vertical attitude. The downwardly inclined attitude of the upper wall induces a laminar flow of the body of a liquid drop 34 along the interior wall surface and, consequently, minimizes both "bouncing" of the drop and excessive "dwelling" of the drop on the upper wall surface. Thus, each drop, after falling on the upper surface of wall 44 is disbursed downwardly in smaller particles 34a into pool 36.

Figure 5:
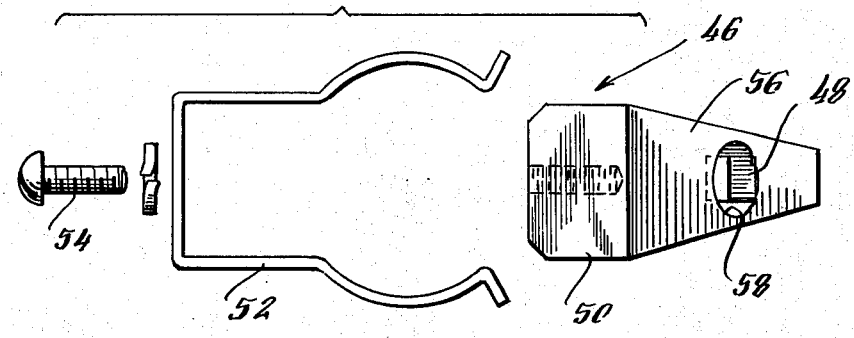
FIG. 5 is an exploded top plan view of the sensor probe and clip.
Figure 4:
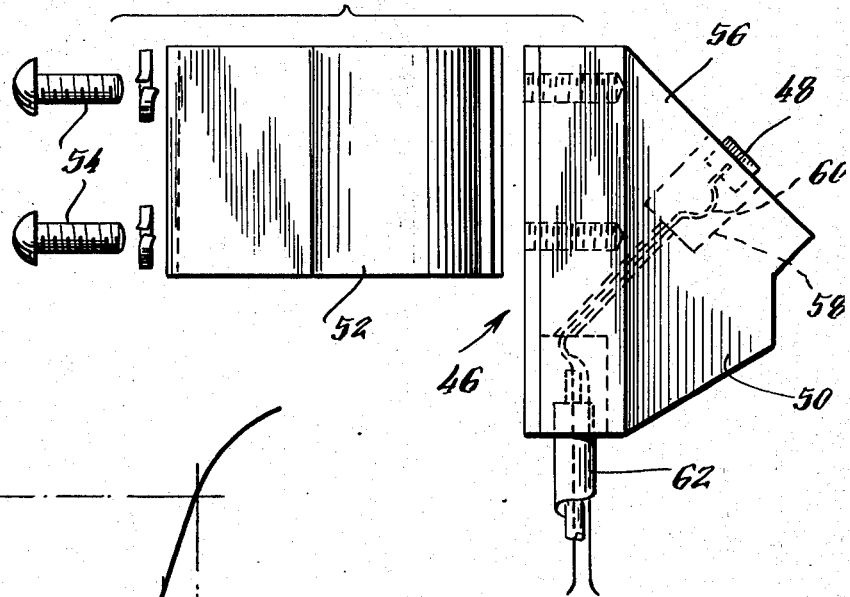
FIG. 4 is an exploded side elevational view of the sensor probe and of a clip for holding the probe in proper engagement with the drip chamber.

Drip chamber indentation 42 (FIGS. 2 and 3) is shaped to accommodate, in interfitting engagement, a sensor probe, generally indicated at 46, which includes a sensor 48 mounted to contact the exterior surface of indentation upper wall 44 (FIG. 2). As shown in greater detail in FIGS. 4 and 5, sensor probe 46 comprises an insulating block 50 that is shaped to exactly compliment the drip chamber indentation 42 and is made from any suitable insulating material such as a plastic sold under the trade name "DELRIN".

The sensor is enclosed in a cylindrical cavity 58 about 0.250 inches deep and about 0.200 inches wide, in insulating block 50 and is mounted to project above the upper block surface 56 which compliments upper indentation wall 44 to further ensure firm contact with the wall. Moreover, the irregular shape of both insulating block 50 and chamber indentation 42 permits their assembly in only one attitude as that sensor 48 properly engages the exterior surface of indentation upper wall 44. Two fine conductive leads 60 extend from sensor 48 through the insulating block 50 to ultimately be enclosed in a cable 62 which is connected to the I.D.T. monitor 40. The sensor is thus connected to provide signals to the monitor as will be described in greater detail below.

A resilient metallic slip 52, attached to insulating block 50 by screws 54, is shaped to removably embrace the drip chamber body 24 and hold insulating block and, hence, sensor in firm engagement with the drip chamber indentation as shown in FIGS. 2 and 3. The sensor probe may, accordingly, be removed from the drip chamber when it becomes necessary to replace the latter for any reason. Since the chamber has no integral electrical components, it is easily manufactured and, therefore, inexpensive. Moreover, the sensor probe can be repeatedly reused even after it becomes necessary to replace the chamber.

Certain characteristics of sensor 48 are important to operation of the present invention. In particular, the sensor is an electrically conductive element, and exhibits conductivity that varies significantly with its temperature. Various devices of this nature are known and include, for example, the type of device generally referred to as a "sensistor". However, in its preferred embodiment, the apparatus of the present invention includes a conductive element from the class of devices known as "thermistors". For reasons set forth below, it is desirable that such a thermistor be of the Positive Temperature Coefficient (PTC) type such as the type manufactured by TDK Electronics Co. Ltd., 14-6, 2-Chome, Uchikanda, Chiyoda-Ku, Tokyo 101, Japan.

At 20° C the nominal resistance of this thermistor model is specified as 23 ohms plus or minus 5%. A probe having this resistance has been found well adapted for use in the present invention. However, it is to be understood that sensors exhibiting resistance widely different from that specified above can be employed provided appropriate adjustments are made in the I.D.T. monitor circuitry.

The sensor probe-drip chamber assembly described above positions thermistor 48 directly in the path of falling drops 34 as can be seen in FIGS. 2 and 3. Since the entire sensor probe including the thermistor is mounted outside of the drop chamber 24, the thermistor 48 is physically as well as electrically isolated from the falling drops. However, upper indentation wall 44, though relatively thick when compared with insulation on many thermistors, is of such thinness in the vicinity of this thermistor 48 as to not isolate it from thermal gradients created by the falling drops. For example, the wall may have thinness of approximately 0.23 to 0.30 millimeters (0.009 to 0.012 inches). Therefore, to the extent that there is any difference between the temperature of the thermistor and the temperature of an impinging drop, thermal exchange between the drop and thermistor will change the thermistor temperature.

Figure 6:
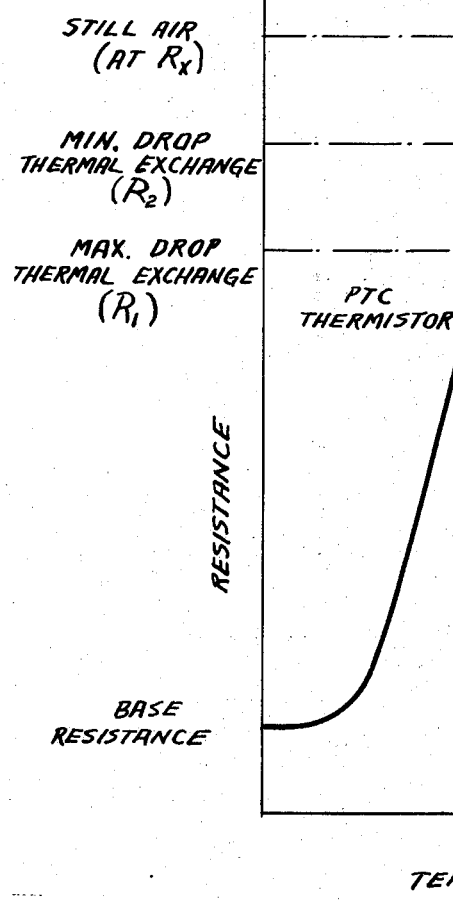
FIG. 6 is a graph of the temperature-resistance characteristics of the electrically conductive element used in the preferred embodiment of the present invention.

It has been found that a PTC thermistor is more effective in delecting these thermal gradients through the relatively thick indentation wall 44 than other types of electrically conductive elements such as Negative Temperature Coefficient (NTC) thermistors. FIG. 6 illustrates the reason for this fact by illustrating a typical resistance-temperature curve of the PTC thermistor device used in the preferred embodiment of the present invention. It its upper operating range, the thermistor exhibits a nearly exponential increase of resistance for linear increase of temperature to which it is exposed. Thus, in its upper operating range, small changes in temperature produce large changes in the resistance exhibited. Therefore, as can be seen in FIG. 6, when a liquid drop has initially impinged on upper wall 44 and minimum thermal exchange has taken place, the thermistor temperature is $T_2$ and resistance is $R_2$. However, when maximum thermal exchange has taken place and temperature falls only a small amount to $T_1$, the thermistor resistance falls a large amount to $R_1$. Since thermal gradients are sensed through the relatively thick upper wall of the chamber indentation (from 0.23 to 0.30 millimeters or 0.009 to 0.012 inches), it is important that the thermistor generate an easily discernable signal as a result of impingement by the partially isolated drop stream. The resistance-temperature characteristic of this thermistor gives this desirable result.

Figure 7:
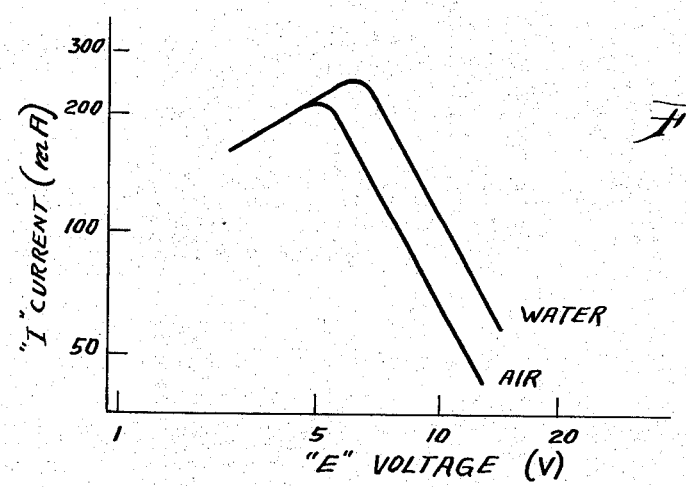
FIG. 7 is a graph of the voltage-current characteristic of the electrically conductive element.

The thermistor of the type described above also has positive volt-ampere operating characteristics which yield the voltage-current curves shown in FIG. 7 for operation in both a water and an air environment. As can be seen, these operating characteristics critically depend upon in which environment the thermistor is located. Specifically, because heat dissipates at a higher rate in the water environment than it does in the air environment, the curve for the water enrironment lies above that for the air environment. Accordingly, application of water or a similar coolant liquid to a thermistor previously immersed in air will, assuming no other conditions change, result in a reduction of terminal voltage.

Figure 8:
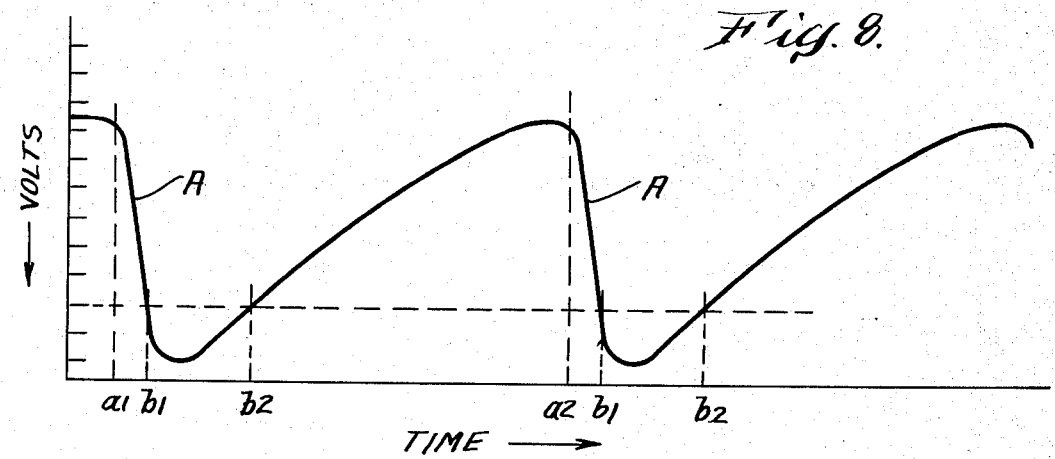
FIG. 8 is a graph of the voltage output of this element versus time when impinged by a stream of falling drops.

This characteristic of a positive temperature coefficient thermistor results in an output response when a sequence of drops fall on the upper surface of indentation wall 44 which is illustrated in FIG. 8. Assuming that points $a_1$ and $a_2$ represent the instant of impingement of successive liquid drops on the upper indentation surface 44 and hence on thermistor 48, and further assuming that the temperature of the thermistor is above the temperature of the liquid drop, the thermistor will first be progressively cooled as the drop impinges upon and envelops the upper indentation wall surface. (As described below, the thermistor is maintained at a high temperature relative to the liquid 12.) The thermistor will then return to its normal temperature as the drop falls off the surface and passes down into the pool 36. During this operation, assuming substantially constant or increasing current flow, the voltage at the leads 60 of thermistor 48 will decline to a minimum in response to the cooling effect and then return to a maximum as the drop flows off the indentation upper wall surface. The resulting oscillatory pulse, illustrated at A in FIG. 8, is utilized by the I.D.T. monitor to control the regulating clamp assembly 38 to, in turn, control the drop rate.

B. The I.D.T. Monitor and Regulating Clamp Assembly

The I.D.T. monitor 40 shown in FIG. 1 incorporates an inventive regulating clamp assembly 38 which is both inexpensive, efficient, yet highly accurate and reliable.

As can be seen in detail in FIGS. 9, 10, and 11, regulating clamp assembly 38 comprises a fixed clamp jaw 64 mounted by means of screws 66 on the front wall 68 of a cabinet 70 which encloses the electronic circuitry of I.D.T. monitor 40. Fixed jaw 64 has a semi-circular cut-out portion 72 having diameter substantially equal to that of the feed tube 14. A second movable jaw 74 is mounted to be reciprocated toward and away from fixed jaw 64 on an adjustment screw 76 and has two opposing wings 78 (FIG. 10) which fit about the lower portion 80 of fixed jaw 74 to guide this reciprocal movement. Further, adjustment screw 76 has a thumb wheel 82 at its outer end, manipulation of which reciprocates the movable jaw toward and away from fixed jaw 64. The movable jaw 74 also has a semi-circular cut-out portion 84 which compliments that disposed in fixed jaw 64 to define a tube supporting channel. Accordingly, when clamped together, the respective jaws are adapted to tightly hold the feed tube in the channel without substantially reducing its diameter.

A plastic pin 86 having a rounded, exposed end is mounted in the fixed jaw 64 for reciprocal movement on an axis perpendicular to the tube supporting channel. This pin, desirably made out of a plastic such as DELRIN plastic, operates to reduce the inside diameter or flow area of the feed tube 14 to thereby increase back pressure in drip chamber 24 as described above.

The plastic pin 86 is operated by an assembly which includes a bimetallic actuator strip 88 mounted in a bracket 90 which is attached to the rear of front wall 68 of cabinet 70. A metal link pin 92, which comprises a threaded bolt 94 tapped into the rear of plastic pin 86 and lock not 96 for locking the respective pins together, interconnects the plastic pin and the bimetallic strip. In particular, the head of bolt 94 abuts the front of bimetallile strip 88. Accordingly, when strip 88 flexes toward the front wall 68 of cabinet 70, plastic pin 86 is pushed toward feed tube 14 to reduce its flow area. However, when strip 88 flexes in the opposite area, the natural resilience of feed tube 14 forces plastic pin 86 backward to increase the tube flow area.

The degree to which the bimetallic strip 88 flexes is determined in conventional fashion by the amount of heat to which it is exposed. A heating coil 98, which may be in the form of a printed circuit coil glued to the rear of strip 88 by a suitable adhesive or which may be wound over the bimetallic strip 88, applies heat thereto when a current is conducted through it from leads 101 and 102. Thus, the amount of current applied to coil 98 determines, through the flexing of bimetallic strip 88, the flow through feed tube 14.

As a safety feature, bimetallic strip 88 is mounted in bracket 90 to flex to increase liquid flow when heat is applied to it. That is, when heat is applied to the strip, it flexes away from plate 68 permitting tube 14 to expand. Conversely, when heat is removed and the strip cools, it flexes toward plate 68 to constrict tube 14 and thereby decrease the drop rate. Accordingly, if a power failure occurs, liquid feed to the patient is cut off.

Figure 12:
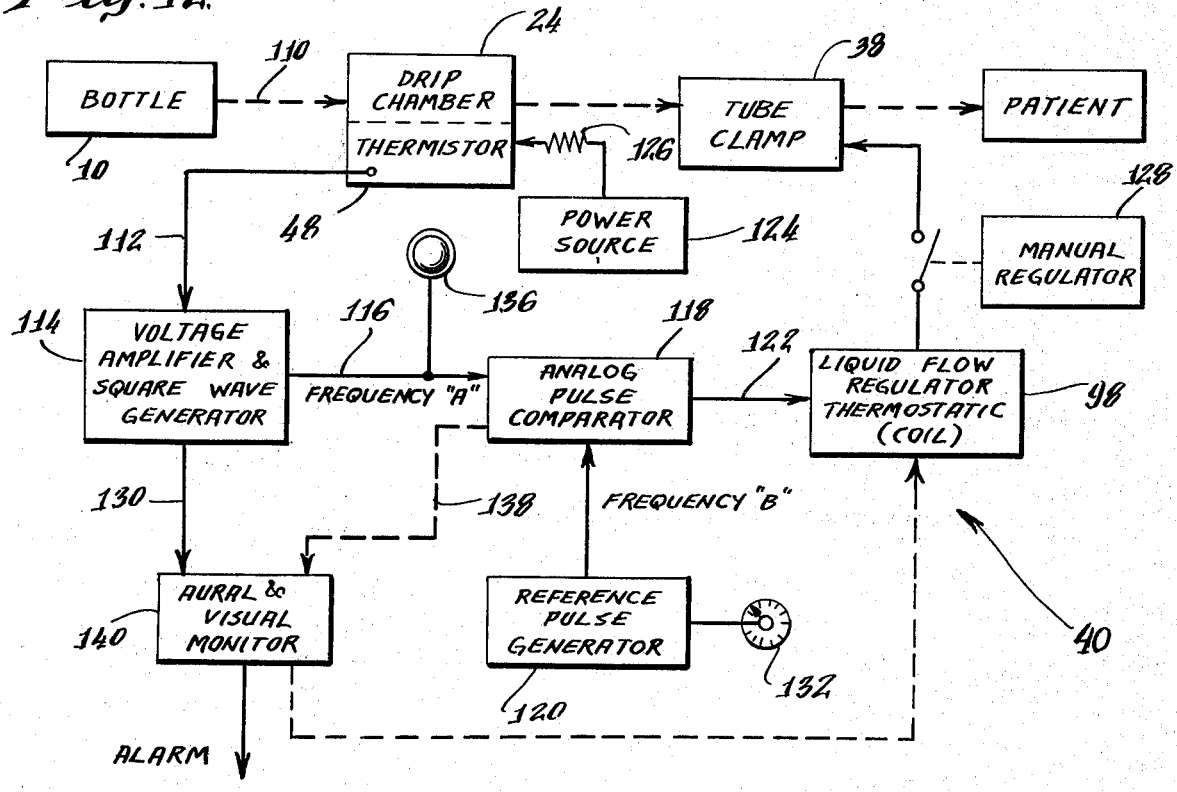
FIG. 12 is a functional block diagram of the apparatus of the present invention.

FIG. 12 illustrates, in diagrammatic form, suitable control apparatus which makes use of the oscillatory signal generated by the thermistor 48 when impinged upon by successively falling drops to control the amount of current supplied to coil 98, to control the amount of heat supplied to the bimetallic strip 88 and to thereby regulate liquid flow through feed tube 14. Liquid flow from the bottle 10 to the drip chamber 24 and, hence, to thermistor 48 is indicated by the dashed line 110. As the liquid in the form of drops impinges upon the upper wall of drip chamber indentation 42, the thermistor, thermally coupled to the drop stream, produces the oscillatory signal or sequence of pulses described with reference to FIG. 8. In accordance with the present invention, these quasi-sinusoidal pulses are converted into steep wave form pulses for application to an analog-digital pulse system. Specifically, the quasi-sinusoidal pulses are applied through a connection 112 to a voltage amplifier and square wave generator 114 which generates an output signal having square wave form with frequency A equal to the frequency of the drops falling in drip chamber 24 when the voltage threshold B of the amplifier is exceeded (see FIG. 8). The output of voltage amplifier and square wave generator 114 is suggested in FIG. 8 by the intervals between the instants $b_1$ and $b_2$.

The frequency A of the square wave output of voltage amplifier and square wave generator 114 is applied along connection 116 to an analog pulse comparator 118 which compares the drop frequency with pulses of frequency B supplied to it by a variable reference pulse generator 120. If the two frequencies are precisely matched, the comparator 118 will produce a ramp signal output current applied along line 122 (coil leads 100 and 102) to the coil 98 to maintain its operating temperature. If, however, frequency A exceeds frequency B, an output control signal will be applied on line 122 to decrease current supplied to coil 98 to thus cool bimetallic strip 88 and increase clamping pressure on feed tube 14. Conversely, if frequency A is less than frequency B, a control signal is applied along line 122 to increase current supplied to coil 98 causing the bimetallic strip to heat up and flex away from feed tube 14 to decrease clamping pressure on the tube. Thus, depending upon the polarity of the energizing signal on line 122, the bimetallic strip 88 may be flexed in either direction to increase or decrease the degree to which feed tube 14 is compressed by plastic pin 86.

With the arrangement described above, the coil 98 will continue to receive periodic energizing signals to flex the bimetallic strip in a given direction as long as a discrepancy continues to exist between the drop frequency A and the reference frequency B supplied by generator 120. By varying clamping pressure on feed tube 14, the average back pressure maintained in drip chamber 24 is correspondingly varied. This adjustment indirectly fixes the rate at which drops will be permitted to form and fall from the drop forming station 28. As soon as the difference between the drop rate and the reference pulse equals zero, energization of the heating coil and thus the degree of flexing of the bimetallic strip 88 reaches a stable condition and all elements of the system remain fixed unless and until a further discrepancy between the signal arises.

The I.D.T. monitor 40 also includes circuitry which comprises a constant D.C. power souce 124 of, for example 15 D.C. volts, which produces, through current limiting resistor 126, a current of about 50 milliamperes across thermistor 48. This current maintains the temperature of thermistor 48 at a level corresponding to its upper temperature operating range. Since the liquid is normally at room temperature, a thermistor temperature of up to 95° C is appropriate. Under these circumstances, impingement of a drop on the upper indentation wall 44 reduces the thermistor temperature temporarily to thereby lower the voltage across the thermistor leads as described with reference to FIG. 8.

As shown in FIG. 1, the I.D.T. monitor 40 is operated by means of controls excessible on the front plate 68 of cabinet 70. A switch 128 is provided to place the I.D.T.

monitor in either automatic or manual mode. When in the manual mode, the drop rate is regulated by adjusting the position of the movable jaw 74 relative to the fixed jaw 64 through action of the thumb wheel 82 and adjustment screw 76. A second switch 130, is provided to control starting and running of automatic operation. When automatic operation is desired, switch 130 is thrown to the "Start" position until the first drop is formed in drip chamber 24, and then changed to the "Run" position. The mode switch 128 is then thrown to the "Auto" position, whereupon the I.D.T. monitor 40 assumes control of the drop rate in chamber 24 as described above.

Further, the control 132 for the reference pulse generator 120 (FIG. 12) is also accessible on the front plate of cabinet 70 (FIG. 1). This control may be set for any of a wide variety of drop frequencies from, for example, 5 to 50 drops per minute.

Certain aural and visual indicators are incorporated in the I.D.T. monitor 40. As shown in FIGS. 1 and 12, an observation lamp 136 is mounted on the face of cabinet 70 and starts flashing continuously and in synchronism with the fluid drop rate which may also be observed through the transparent body of drip chamber 24. However, if liquid in bottle 10 becomes exhausted so that no drops develop at drop forming station 28, an alarm signal is transmitted along connection 138 to an aural and visual monitoring circuit 140 indicated diagrammatically in FIG. 12. This monitor generates either an aural or visual signal at a nurse's station to indicate that empty bottle 10 must be replaced with a full one. Simultaneously, a signal from the aural and visual monitoring circuit 140 to coil 98 causes pin 86 to completely close fluid feed tube 14. This action stops further flow of liquid through the system and thus prevents entry of air into the patient's cardiovascular system. Further, light 136 stops flashing and stays out.

Other out-of-limit condition indicators may be incorporated into the I.D.T. monitor 40. For example, these indicators may function during a power outage of other selected malfunctions of the system.

It can be appreciated from the above description that the I.D.T. monitor incorporates an inventive regulating clamp assembly, including the bimetallic strip 88 and heating coil 98, for regulating flow of liquid through feed tube 14. This assembly is simple and much less expensive than certain prior art apparatus. However, this regulating clamp assembly is extremely accurate.

Although a specific embodiment of the present invention has been described above in detail, it is to be understood that this is for purposes of illustration. Modifications may be made to the described structures by those skilled in the art in order to adapt this drop sensing and regulating apparatus to particular applications.

What is claimed is:

1. An apparatus for sensing and regulating the rate at which liquid drops fall along a predetermined vertical path, said apparatus comprising:
    A. an enclosure which defines a vertical drop path and which is formed with an indentation having a wall portion that projects directly into the drop path to be impinged by drops falling therealong;
    B. a probe removably mounted on the exterior of said enclosure in said enclosure indentation and including an electrically conductive element located to contact the exterior surface of said indentation wall portion which is directly in the drop path, the conductivity of said element being significantly variable with its temperature, said indentation wall portion being of such thinness in the vicinity of said conductive element as not significantly to isolate said element from thermal gradients created by drops falling successively on said wall portion; and
    C. means electrically connected to said conductive element for regulating the rate at which drops fall along the drop path in response to changes in conductivity of said element caused by thermal gradients created by drops falling on said indentation wall portion.

2. The apparatus for sensing and regulating the rate at which liquid drops fall along a predetermined vertical path as claimed in claim 1 wherein said enclosure indentation wall portion is inclined to minimize bouncing as well as dwell of drops that impinge on it.

3. The apparatus for sensing and regulating the rate at which liquid drops fall along a predetermined vertical path as claimed in claim 1 wherein said probe further comprises:
    an insulating block in which said conductive element is mounted, said block having shape complimentary to said enclosure indentation; and
    means for removably holding said block in said enclosure indentation with said electrically conductive element in contact with the exterior surface of said indentation wall portion.

4. The apparatus for sensing and regulating the rate at which liquid drops fall along a predetermined vertical path as claimed in claim 1 wherein said conductive element is a thermistor.

5. The apparatus for sensing and regulating the rate at which liquid drops fall along a predetermined vertical path as claimed in claim 4 wherein said thermistor is of the Positive Temperature Coefficient type.

6. The apparatus for sensing and regulating the rate at which liquid drops fall along a predetermined vertical path as claimed in claim 1 further comprising means for maintaining said conductive element at an average temperature above the predictable temperature of the falling drops.

7. The apparatus for sensing and regulating the rate at which liquid drops fall along a predetermined vertical path as claimed in claim 1 wherein liquid is conducted from the bottom of said enclosure in a flexible, pliable tube and wherein said drop rate regulating means regulates liquid back pressure in said enclosure and comprises:
    A. fixed support means for holding said tube,
    B. clamp means movable relative to said support means to compress said tube, reduce its inside cross-sectional area and, hence, reduce liquid flow therethrough; and
    C. means for adjustably moving said clamp means toward said support means, said moving means including
        1. a bimetallic strip, operatively associated with said clamp means, which flexes to a degree related to the heat applied to said strip, and
        2. means electrically connected to said conductive element for applying heat to said bimetallic strip to operate said clamp means and regulate flow through said tube and back pressure in said enclosure to regulate the drop rate.

8. The apparatus for sensing and regulating the rate at which liquid drops fall along a predetermined vertical path as claimed in claim 7 wherein said heat applying means comprises a heating coil in the form of a printed circuit coil which is attached to said bimetallic strip.

9. The apparatus for sensing and regulating the rate at which liquid drops fall along a predetermined vertical path as claimed in claim 7 wherein said heat applying means comprises a heating coil in the form of a wire coil wound about said bimetallic strip.

10. An apparatus for sensing the rate at which liquid drops fall along a predetermined vertical path and for regulating the drop rate to be substantially equal to a preselected drop rate, said apparatus comprising:
   A. an enclosure which defines a vertical drop path;
   B. an electrically conductive element associated with said enclosure and positioned directly in the drop path, the conductivity of said element being significantly variable with its temperature;
   C. means for insulating said conductive element and electrically isolating it from falling drops, without significantly isolating said element from thermal gradients created by drops falling on it, said conductive element thereby being thermally coupled to the falling drops to sense the drop rate;
   D. A flexible, pliable tube connected to the bottom of said enclosure for conducting liquid therefrom; and
   E. means for regulating liquid back pressure in said tube and said enclosure to thereby regulate the rate at which drops fall along the drop path, said regulating means comprising:
      1. fixed support means for holding said tube;
      2. clamp means mounted for movement toward said support means to compress said tube, reduce its cross-sectional area and, the liquid flow therethrough;
      3. means, for moving said clamp means toward said support means, comprising:
         a. a bimetallic strip which flexes to a degree related to the heat applied to it, said strip being operatively associated with said clamp means, and
         b. means for applying heat to said bemetallic strip; and
      4. monitor means for comparing the drop rate sensed by said conductive element with the preselected drop rate and for controlling said heat applying means and, hence, said bimetallic strip to regulate back pressure to said enclosure until the sensed drop rate is substantially equal to the preselected drop rate.

11. The apparatus for sensing the rate at which liquid drops fall along a predetermined vertical path and for regulating the drop rate to be substantially equal to a preselected drop rate as claimed in claim 10 wherein said tube support means comprises:
   A. a fixed jaw; and
   B. a movable jaw mounted to be closed against said fixed jaw, said fixed and movable jaws defining a tube supporting channel having cross-sectional shape and size substantially the same as said tube.

12. The apparatus for sensing the rate at which liquid drops fall along a predetermined vertical path and for regulating the drop rate to be substantially equal to a preselected drop rate as claimed in claim 10 wherein said clamp means comprises
   a pin having a blunt end for abutting said tube and being mounted for reciprocal axial movement in a direction transverse to the axis of said tube when held in said support means, to compress the side wall of said tube to reduce its inside cross-sectional area,
   said bimetallic strip being mounted to contact the end of said pin opposite said blunt end with said pin extending transversely from the plane of said strip whereby flexing of said strip causes reciprocal axial movement of said pin.

13. The apparatus for sensing the rate at which liquid drops fall along a predetermined vertical path and for regulating the drop rate to be substantially equal to a preselected drop rate as claimed in claim 12 wherein said bimetallic strip is mounted at its ends so that flexing bows its center and wherein said pin contacts said strip intermediate its ends.

14. The apparatus for sensing the rate at which liquid drops fall along a predetermined vertical path and for regulating the drop rate to be substantially equal to a preselected drop rate as claimed in claim 10 wherein said heat applying means comprises a heating coil in the form of a printed circuit coil which is attached to at least one face of said bimetallic strip.

15. The apparatus for sensing the rate at which liquid drops fall along a predetermined vertical path and for regulating the drop rate to be substantially equal to a preselected drop rate as claimed in claim 10 wherein said heat applying means comprises a heating coil in the form of a wire coil wound about said bimetallic strip.

16. The apparatus for sensing the rate at which liquid drops fall along a predetermined vertical path and for regulating the drop rate to be substantially equal to a preselected drop rate as claimed in claim 10 wherein said enclosure is formed with an indentation having a wall portion that projects directly into the drop path to be impinged by drops falling therealong, said wall portion comprising said insulation means and wherein said apparatus further comprises
   a probe mounted on the exterior of said enclosure in said enclosure indentation, said electrically conductive element being located in said probe to contact the exterior surface of said indentation wall portion.

17. The apparatus for sensing the rate at which liquid drops fall along a predetermined vertical path and for regulating the drop rate to be substantially equal to a preselected drop rate as claimed in claim 16 wherein said enclosure indentation wall portion is inclined downwardly to minimize bouncing as well as dwell of drops that impinge on it.

18. The apparatus for sensing the rate at which liquid drops fall along a predetermined vertical path and for regulating the drop rate to be substantially equal to a preselected drop rate as claimed in claim 16 wherein said probe further comprises:
   an insulating block in which said conductive element is mounted, said block having shape complimentary to said enclosure indentation; and
   means for removably holding said block in said enclosure indentation with said electrically conductive element in contact with the exterior surface of said indentation wall portion.

19. The apparatus for sensing the rate at which liquid drops fall along a predetermined vertical path and for regulating the drop rate to be substantially equal to a preselected drop rate as claimed in claim 10 wherein said conductive element is a thermistor.

20. The apparatus for sensing the rate at which liquid drops fall along a predetermined vertical path and for regulating the drop rate to be substantially equal to a preselected drop rate as claimed in claim 19 wherein said thermistor is of the Positive Temperature Coefficient type.

* * * * *